United States Patent

Kaneko et al.

[11] Patent Number: 5,128,102
[45] Date of Patent: Jul. 7, 1992

[54] PROBE FOR MEASURING OXYGEN CONCENTRATION

[75] Inventors: Masao Kaneko, Tokyo; Hideki Nakamura, Fujinomiya, both of Japan

[73] Assignees: Terumo Kabushiki Kaisha, Tokyo; Rikagaku Kenkyusho, Wako, both of Japan

[21] Appl. No.: 295,596

[22] PCT Filed: Jul. 3, 1987

[86] PCT No.: PCT/JP87/00463
§ 371 Date: Jan. 3, 1989
§ 102(e) Date: Jan. 3, 1990

[87] PCT Pub. No.: WO88/00339
PCT Pub. Date: Jan. 14, 1988

[30] Foreign Application Priority Data

Jul. 3, 1986 [JP] Japan .................... 59-157033

[51] Int. Cl.$^5$ .................... G01N 21/64; G01N 33/52
[52] U.S. Cl. .................... 422/56; 422/52; 422/82.06; 422/82.07; 422/82; 422/08; 422/86; 250/459.1; 250/461.1; 356/317
[58] Field of Search .................... 422/52, 55, 56, 88, 422/82.06–82.08, 86; 436/136, 172, 68, 138; 252/301.26, 408.1; 250/458.1, 459.1, 461.1; 356/41, 317, 318

[56] References Cited

U.S. PATENT DOCUMENTS 4,721,669  1/1988  Barton .................... 435/6
4,772,707  9/1988  Hammon et al. .................... 546/2
4,880,752  11/1989  Keck et al. .................... 435/7

FOREIGN PATENT DOCUMENTS 60-63464   4/1985  Japan .
62-30959   2/1987  Japan .
2132348A   7/1984  United Kingdom .

OTHER PUBLICATIONS

*Russian Chemical Reviews,* vol. 41, No. 11, Nov., 1972, pp. 991–1008, London, GB; A. T. Philipenko et al., "Analytical Chemistry of Metal Complexes with Nitrogen-containing Ligands of the 2,2' bipyridyl type".

*Primary Examiner*—James C. Housel
*Assistant Examiner*—David Redding
*Attorney, Agent, or Firm*—Oblon, Spivak, McClelland, Maier & Neustadt

[57] ABSTRACT

A probe for measuring oxygen concentration including an immobilized polypyridine metal complex, which can be used for measurement of oxygen concentration even in a case where the exciting ray to be used and luminescence are visible rays and which can stably be used even when it is directly immersed in a liquid to be examined without a protective membrane, which makes miniaturization of a probe possible.

7 Claims, 4 Drawing Sheets

PROBE FOR MEASURING OXYGEN CONCENTRATION

BACKGROUND OF THE INVENTION

1. Field of the Invention

The present invention relates to a probe for measuring the oxygen concentration in a solution or a gas by utilizing quenching by oxygen of luminescence following excitation by light.

2. Description of the Prior Art

Heretofore, as for a method for measuring the oxygen concentration in an aqueous solution, there has generally and widely been used an electrochemical method in which an oxygen electrode represented by Clark type one is used and reduction current of oxygen is measured under a controlled electric potential. However, in this method, since an electric current which flows between two electrodes is measured, the current density cannot be so diminished, and therefore miniaturization of the electrodes to be used is limited. Further, an electric current is generated even in a small extent, and thus it is not proper from the safety aspect to use the method, for example in vivo or in a blood vessel.

In view of these problems, various methods utilizing light for measuring oxygen concentration have been proposed. Since it was reported that pyrenebutyric acid is effective as a fluorescent probe for measuring oxygen concentration (W. M. Vaugham and G. Weber, Biochem, 9, 464 (1970)), many researches have been conducted on probes utilizing quenching by oxygen of fluorescence from derivatives of pyrene. Further, another device utilizing pyrenebutyric acid was made (N. Opitz and D. W. Lubbers, Z. Biomed. Techn. 28 (31), (1983)). However, in this method it is necessary to use an ultraviolet ray as the exciting ray, so that materials which transmit an ultraviolet ray must be used in the optical system such as a conductor of the exciting ray. When a probe comprising perylene dibutyrate adsobed on silica gel is used, a visible ray (wave length of 468 nm) can be used as the exciting ray (J. I. Peterson, R. V. Fitzgerald and D. K. Buckhold, Anal. Chem. 56, 62 (1984)). However, since this probe greatly suffers from water, it is necessary to protect it with a hydrophobic and oxygen-permeable membrane, which makes the miniaturization thereof more difficult. Thus, there has not hitherto been a probe for measuring oxygen concentration where the exciting ray and luminescence are visible rays and which can stably be used even when it is directly immersed in a liquid to be examined without a protective membrane such as an oxygen-permeable membrane thereon.

SUMMARY OF THE INVENTION

Accordingly, an object of the present invention is to provide a probe for measuring oxygen concentration, which can be used in a method for measuring oxygen concentration using light but not using an electrochemical method, where the exciting ray and luminescence are visible rays, so that a flexible plastic optical fiber and the like can be used as the conduction of light and also inexpensive materials for visible rays can be used in the optical system, and which can stably be used even when it is directly immersed in a solution and the like without a protective membrane such as an oxygen-permeable membrane, which makes the miniaturization thereof easier.

It has been found that the above object of the present invention is attained by a probe for measuring oxygen concentration comprising an immobilized polypyridine metal complex.

BRIEF DESCRIPTION OF THE DRAWINGS

In FIG. 1, 1 represents a quartz plate, 2 represents a fixed membrane of a polypyridine metal complex, 3 represents a quartz cell, and 4 represents a holder made of rubber.

DETAILED DESCRIPTION OF THE INVENTION

In the above-described, the probe means any form of instrument for measuring oxygen concentration comprising an immobilized polypyridine metal complex, including a probe made by molding an immobilized polypyridine metal complex into a desired shape, a probe made by forming a thin film of an immobilized polypyridine metal complex on the surface of a desirably shaped support such as a later-described styrene or silicone flexible plastic optical fiber, and a probe made by adsorbing a polypyridine metal complex on a desirably shaped support to immobilize the same. Thus, by immobilizing a polypyridine metal complex and measuring the intensity of luminescence thereof, it is possible to know the oxygen concentration in a solution above all an aqueous solution or in a gas. A polypyridine metal complex is soluble in water or readily dispersible in water, and cannot stably be used as such in water as a probe for measuring oxygen concentration.

The present inventors have found that the intensity of the visible luminescence generated by irradiating an immobilized polypyridine metal complex with a visible ray depends on the oxygen concentration in a solution or a gas which is in contact with the complex, and that the relation between the luminescence intensity and the oxygen concentration is represented by the following equation:

$$Io/I = 1 + K(O_2) \qquad (1)$$

wherein Io and I are respectively luminescence intensities, provided that Io is the luminescence intensity when the oxygen concentration is substantially 0, K is a constant, and ($O_2$) is the oxygen concentration. Since Io and K are constants independent of the oxygen concentration in materials to be examined, it is possible to known the oxygen concentration by measuring the luminescence intensity I.

Various methods are applicable for immobilization of the polypyridine metal complex. Conditions for the immobilization include, (1) that the immobilized metal complex does not dissolve in the liquid to be examined (If dissolved, the luminescence intensity changes, which makes the measurement thereof difficult), (2) that the immobilized metal complex does not suffer an irreversible change by a chemical reaction with the liquid or gas to be examined, and so on.

First, the polypyridine metal complex may most simply be immobilized by dissolving or dispersing the same in a macromolecule.

Many kinds of macromolecules can be used for this purpose. Especially preferred macromolecules include many general purpose plastic usually used such as low density polyethylenes, polypropylenes, polyvinyl chlorides, ethylene-vinyl acetate copolymers, polystyrenes, polymethyl methacrylates, silicone resins and polyurethanes. A specific method for introducing the polypyridine metal complex into such a macromolecules is conveniently selected according to the kind of macromolecule to be used. For example, there can be used mixing by fusion with heating in case of thermoplastics having a high solvent resistance such as a low density polyethylene, and mixing in a solution (mixing in a solution of a macromolecule in an organic solvent) in case of polystyrene and the like. Proper concentration of the polypyridine metal complex in the mixture with the macromolecule is $1 \times 10^{-8}$ to 1 mol/dm$^3$. In the concentration less than $10^{-8}$ mol/dm$^3$ adequate luminescence cannot be obtained and thus the sensitivity is inadequate. On the other hand, in the high concentration exceeding 1 mol/dm$^3$, the luminescence intensity does not change in accordance with the oxygen concentration and the probe is not fit for use.

The second method is one in which the polypyridine metal complex is made to be chemically or physically adsorbed on an adsorbent. The adsorbent includes inorganic materials such as silica gels and glasses, organic materials such as porous polymers, various ion exchange resins, and natural materials e.g. polysaccharides and proteins. A cation exchange resin or a chelate type adsorbent can be used to make fixation more stable.

The third method is one in which the polypyridine metal complex is introduced in a macromolecule as a constitutive unit thereof to make a physically and chemically more stable immobilized complex. Although this process requires somewhat complicated procedures compared with the above two methods, it is possible to obtain an immobilized material having the highest stability. Specifically, there may be adopted a method where a polypyridine having a polymerizable functional group is polymerized or copolymerized with a monomer capable of copolymerizing therewith to obtain a polymer or copolymer, and then a metal complex is formed, for example a method where a vinyl compound such as styrene, methacrylic acid, acrylic acid or acrylonitrile is copolymerized with a polypyridine (a ligand) having a vinyl group such as 4-methyl-4'-vinyl-2,2'-bipyridine, and then a metal complex is formed; a method where a monomer having a functional group which is capable of chemically bonding with a substituent of the polypyridine metal complex is polymerized in advance, and then the substituent is bonded to the functional group; and the like. In this connection, the copolymer includes random copolymers, block copolymers, graft copolymers, polymers bridged with the complex and the like.

Proper molar ratio of the monomer to the complex is 1000 to 1, although it is also possible to use the complex only.

It is possible to combine two or more of the above methods. For example, it is also possible to mix the macromolecular complex with another macromolecule.

It is preferable that the polypyridine metal complex is immobilized on a conductor of a visible ray such as a flexible plastic optical fiber.

Thus, in order to obtain the immobilized polypyridine metal complex which is chemically or physically more stable, it is preferable that the polypyridine, which is a ligand, is selected from bipyridine, phenanthroline, terpyridine and derivatives thereof. The derivatives are intended to mean a derivative where one or more of hydrogens in the pyridine ring of these polypyridine are independently substituted with other groups, for example alkyl groups, vinyl groups, acetyl groups, halogens, hydroxyl groups or phenyl groups.

Further, it is preferable that the metal in the polypyridine metal complex is a transition metal. Preferable transition metal includes ruthenium, osmium, chromium, iridium, iron, cobalt, europium and the like, and ruthenium is the most desirable. The highest sensitivity is obtained when ruthenium is incorporated. For example, tris(2,2'-bipyridine)ruthenium (II) complex has the absorption maximum of 452 nm, the luminescence maximum of 605 nm and the strong luminescence intensity, and thus is preferably used in the present invention. When this compound is incorporated into a macromolecule, these properties of this complex are hardly changed, and thus the complex may effectively be used. However, other transition metals may also adequately be used.

The following are examples of the present invention.

EXAMPLE 1

γ-Picoline (Manufactured and sold by Kanto Kagaku Co., Ltd., EP grade reagent) was purified by distillation, and used to prepare 4-methyl-4'-vinyl-2,2'-bipyridine (hereinafter referred to as "Vbpy") according to the known method (P. K. Ghosh and T. G. Spiro, J. Am. Chem. Soc., 102, 5543 (1980)). The Vbpy was purified by a column chromatography (silica gel 40 to 100 mesh, solvent: chloroform/methanol (5/1), both solvents are guaranteed reagents manufactured and sold by Wako Pure Chemical Industries, Ltd ). 0.49 g (2.5 mmol) of this Vbpy and 5 g (50 mmol) of methyl methacrylate (hereinafter referred to as "MMA") which had been subjected to high vacuum distillation in advance were copolymerized in 50 ml of 1,4-dioxane (guaranteed reagent manufactured and sold by Wako Pure Chemical Industries, Ltd.) in the presence of 0.08 g (0.5 mmol) of α,α'-azobisisobutyronitrile (GR grade reagent manufactured and sold by Kanto Chemical Co., Ltd., hereinafter referred to as "AIBN") (in a polymerization tube deaerated and plugged at 60° C. for 5 days). One g of the obtained copolymer and 0.15 g of cis-dichlorobis(bipyridine)ruthenium complex (hereinafter referred to as "cis-Ru(bpy)$_2$ Cl$_2$·4H$_2$O") synthesized and purified according to the known method (G. Sprintschnik, H. W. Sprintschnik, P. P. Kirsch and D. G. Whitten, J. Am. Chem. Soc., 99, 4947 (1977)) were reacted in 700 ml of 1-butanol (guaranteed reagent manufactured and sold by Kanto Chemical Co., Ltd.) under reflux (for 24 hours). The product was evaporated to dryness, extracted with chloroform (guaranteed reagent) and evaporated to dryness again to obtain the final product A.

Elementary analysis showed that the product A is a copolymer having the following structure.

20

Figure 1:
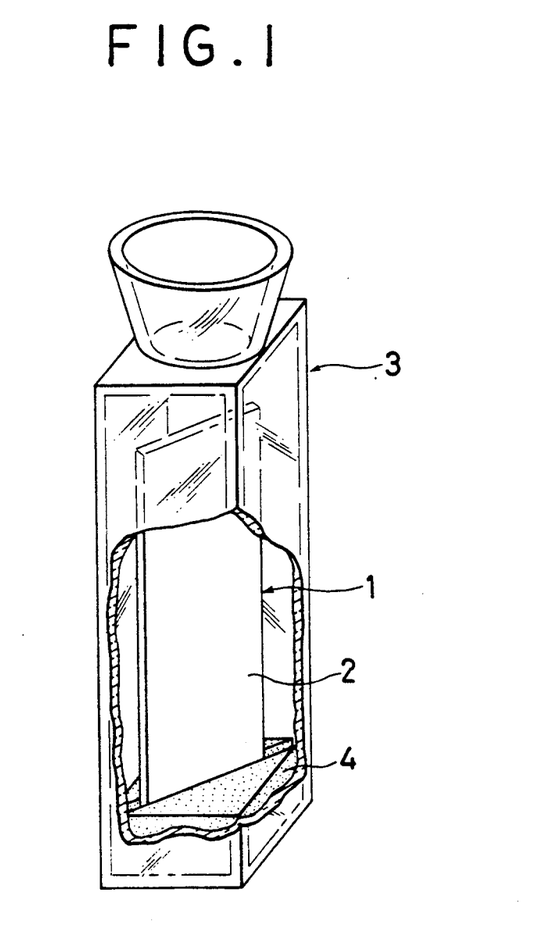
FIG. 1 is a drawing illustrating an instrument for measuring the luminescence intensity of a probe for measurement of oxygen concentration.

A 10% methanol solution of this macromolecular complex was added dropwise on a rectangular quartz plate 1 (thickness 1 mm, length 40 mm, width 8 mm), followed by deaeration and drying while the plate was held horizontal to obtain a transparent reddish orange membrane 2 of the thickness of about 10 μm. The membrane 2 was washed several times with flowing water and held in a whole surface transparent quartz cell 3 (optical path length 1 cm) equipped with a ground-in stopper with a holder 4 made of rubber as shown in FIG. 1, and the cell was filled with physiological saline (a 0.9% aqueous sodium chloride solution).

Figure 2:
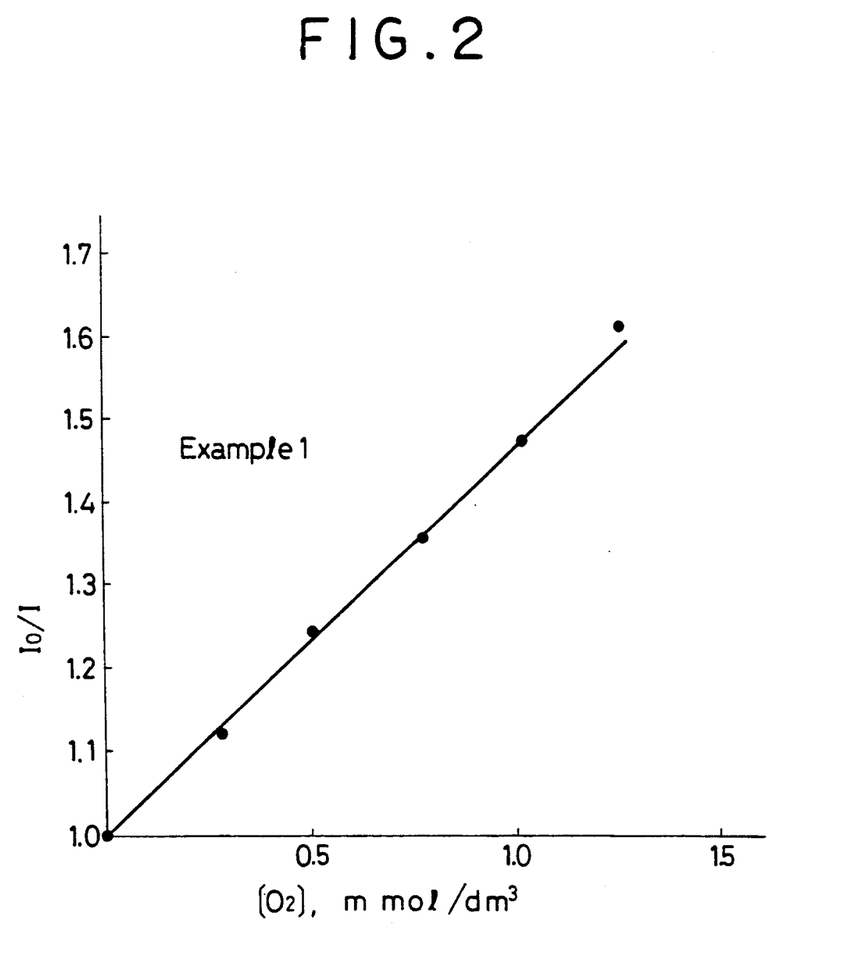
FIGS. 2 and 3 are drawings illustrating the relation between the oxygen concentration and the luminescence intensity in a solution to be examined using a probe for measurement of oxygen concentration of the present invention.

Argon gas (purity 99.9%) or oxygen gas (purity 99.5%) or a mixed gas thereof (The concentration ratio was made to be arbitrarily set up by the method in which the flow rate ratio is changed) was introduced into the physiological saline in the cell at the flow rate of 50 cc/min for 15 minutes to cause bubbling, whereby the oxygen concentration in the physiological saline was arbitrarily set up from zero to saturation. In this connection, the relation between the mixing ratio of argon/oxygen and the oxygen concentration in the aqueous solution was determined in advance by an oxygen electrode (M-HOS ® $PO_2$ sensor manufactured and sold by Mitsubishi Rayon Co., Ltd.). It was found that a linear relation exists between the oxygen/argon mixing ratio and the oxygen concentration, and the oxygen concentration at the saturation is $1.26 \times 10^{-3}$ mol/dm$^3$. The cell was tightly plugged immediately after the gas bubbling, and the luminescence intensity was measured by a luminescence spectrophotometer (MPF-4 type, manufactured and sold by Hitachi, Ltd.). In the measurement, an exciting ray having the wave length of 460 nm was used and the luminescence was measured at the wave length of 610 nm. Both gas bubbling and measurement of luminescence were conducted at 22° C. The results are shown n Table 1. Linear relation exists between Io/I and the oxygen concentration as shown in FIG. 2, and thus it is seen that the membrane 2 can be used as a probe for measuring oxygen concentration.

TABLE 1

Relation between the oxygen concentration and the luminescence intensity (Example 1)

| Oxygen concentration | | Luminescence intensity | |
|---|---|---|---|
| Introduced gas (%) | In physiological saline[*1] | (mm)[*2] | Io/I |
| 0 | 0 | 127.8 | 1.000 |
| 22.7 | 0.287 | 113.9 | 1.122 |
| 40.4 | 0.512 | 102.6 | 1.246 |
| 62.0 | 0.785 | 94.3 | 1.355 |
| 81.2 | 1.03 | 86.9 | 1.471 |
| 99.5 | 1.26 | 79.4 | 1.610 |

[*1] Unit mmol/dm$^3$
[*2] Sensitivity 30 + 5 Scale height at the recorder range of 5 mV

EXAMPLE 2

Tris(bipyridine)ruthenium complex (hereinafter referred to as "Ru(bpy)$_3$Cl$_2$") was obtained from ruthenium chloride anhydride (reagent manufactured by Aldrich Corporation) and bipyridine (reagent manufactured by Aldrich Corporation) according to the known method (C. T. Lin, W. Bottchem, and M. Chou, J. Am. Chem. Soc., 98, 6536 (1976)). This metal complex was weighed so that the concentration after mixing became $10^{-3}$ mol/dm$^3$, and well mixed with the silicone sealant of a room temperature cross-linking type (SE5001 manufactured by Toray Silicone Co., Ltd.). The mixture was coated on the same quartz plate 1 as that used in Example 1 so that an almost uniform membrane having the thickness of about 0.1 mm was formed. The resulting plate was allowed to stand horizontally in an oven (60° C.) for 30 minutes to harden the membrane, whereby a silicone membrane containing Ru(bpy)$_3$Cl$_2$ was obtained. After the membrane was several times washed with flowing water, the relation between the oxygen concentration and the luminescence intensity was determined under immersion thereof in physiological saline in the same manner as in Example 1. As a result, a good linear relation between Io/I and the oxygen concentration was obtained.

EXAMPLE 3

A copolymer of styrene and Vbpy was obtained in the same manner as in Example 1, and subjected to the same reaction as in Example 1 for forming a complex with ruthenium, whereby the following macromolecular complex B was obtained.

Figure 3:
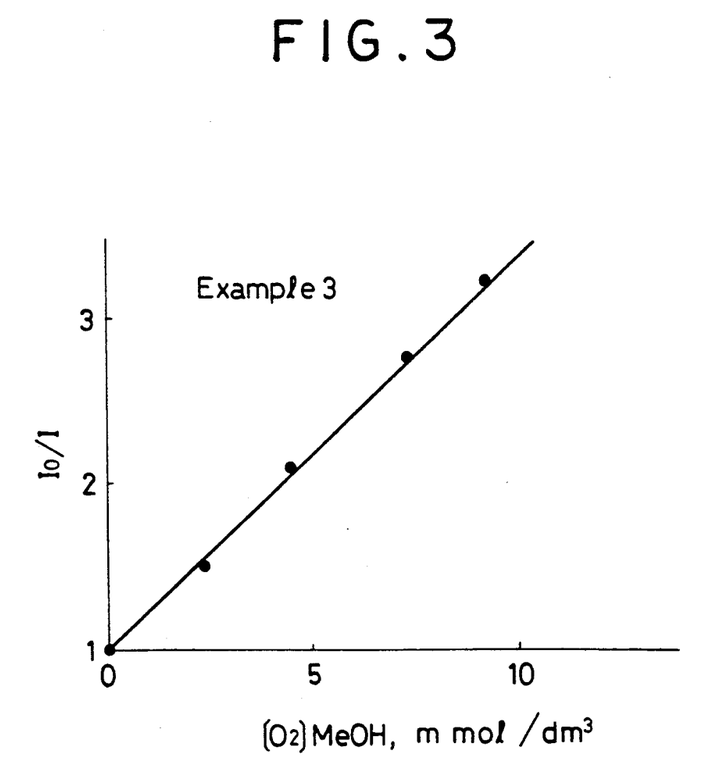
Figure 4:
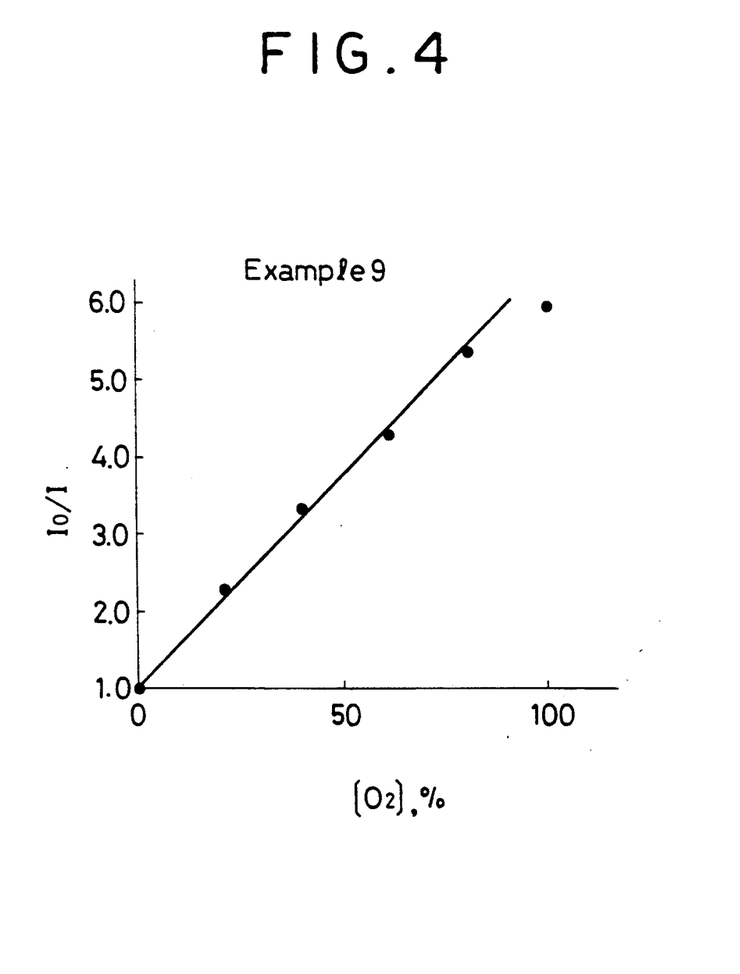
FIG. 4 is a drawing illustrating the relation between th oxygen concentration and the illuminescence intensity in a gas to be examined using a probe for measurement of oxygen concentration of the present invention.

Then, an orange translucent membrane having the thickness of about 10 μm was formed on a quartz plate using the complex B in the same manner as in Example 1. The membrane was set up in the cell 3 for measuring luminescence in the same manner as in Example 1, the cell was filled with methanol (guaranteed reagent, manufactured and sold by Wako Pure Chemical Industries, Ltd.) in place of physiological saline in Example 1. The oxygen concentration in methanol was arbitrality set and the relation between the oxygen concentration and the luminescence intensity was investigated. As a result, good linear relation was found between Io/I and the oxygen concentration (Refer to FIG. 3). The concentration at oxygen saturation was supposed to be 9.45 mmol/dm$^3$ ("Kagaku Binran Kisohen II" (Chemical Handbook Fundamental Volume II) edited by The Chemical Society of Japan, p. II-164).

EXAMPLE 4

A 10 mM aqueous solution of Ru(bpy)$_3$Cl$_2$ which had been synthesized and purified in Example 2 was prepared. A Nafion 117 ® membrane (thickness of 0.007 inches, sold by Aldrich Corporation) which is a cation exchanger was immersed in the solution for 10 hours, taken out therefrom, washed several times with water and dried at room temperature for 24 hours to obtain an orange Nafion ® membrane which adsorbed Ru(bpy)$_3$$^{2+}$. This membrane was stuck on the same quartz plate as in Example 1 with a pressure sensitive adhesive double-coated type. The resulting plate was fixed in a cell in the same manner as in Example 1 and the relation between the luminescence intensity and the oxygen concentration in physiological saline was determined. Good linear relation was found between Io/I and the oxygen concentration.

EXAMPLE 5

Vbpy and acrylic acid (guaranteed reagent, manufactured and sold by Wako Pure Chemical Industries, Ltd. and distilled under high vacuum) were copolymerized in the same manner as in Example 1, and cis-Ru(bpy)$_3$Cl$_2$ was reacted with the resulting copolymer to obtain a macromolecular complex C of the following formula:

Purification was carried out by dialysis of an aqueous solution thereof (48 hours). A 5% methanol solution of this macromolecular complex was prepared, and Nafion 117 ® was immersed therein, washed with water, dried and used for measurement of the luminescence intensity in physiological saline in the same manner as in Example 4, except that measurement of the luminescence was conducted at 610 nm. The results revealed a good linear relation between Io/I and the oxygen concentration.

EXAMPLE 6

Tris(1,10-phenanthroline)ruthenium complex perchlorate trihydrate (hereinafter referred to as "Ru(phen)$_3$(ClO$_4$)$_2$·3H$_2$O" was synthesized and purified according to the known method (C. T. Lin, et al., J. Am. Chem. Soc., 98, 6536 (1976)). A chelate filter paper having an iminodiacetic acid group (manufactured and sold by Sumitomo Chemical Co., Ltd.) was immersed in a 10 mM aqueous solution thereof (10 hours), washed with water and dried to obtain a chelate paper on which Ru(phen)$_3$$^{2+}$ was adsorbed. This paper was fixed in cell 3 and the luminescence intensity in physiological saline was measured, in the same manner as in Example 4, except that the wave length of the exciting ray was 450 nm and measurement of the luminescence was conducted at the wave length of 600 nm. A good linear relation was found between Io/I and the oxygen concentration, as was found in the preceding examples.

EXAMPLE 7

According to the same method as in Example 1, 2-hydroxyethyl methacrylate (EP grade reagent, manufactured and sold by the Kanto Chemical Co., Ltd., hereinafter referred to as "HEMA") as subjected to high vacuum distillation in advance and Vbpy were copolymerized, and the resulting copolymer was reacted with cis-Ru(bpy)$_2$Cl$_2$ to obtain the macromolecular complex D of the following formula:

A 1 mmol/dm$^3$ (based on Ru) aqueous solution of this macromolecular complex was prepared, and gelatin (reagent manufactured by Aldrich Corporation) derived from pig hides was added to this solution to make the concentration of 10%. The mixture was heated to dissolve the gelatin, poured in a laboratory dish (made of glass, 15 mm$\phi$) which was horizontally held, cooled, solidified, and dried in a desiccator. The thus obtained gelatin membrane (thickness of about 0.1 mm) containing the macromolecular complex D was cut into a size 40 mm long and 8 mm wide, and fixed on quartz plate 1 through a pressure sensitive adhesive double-coated tape. The relation between the luminescence intensity and the oxygen concentration in physiological saline was investigated, and the results revealed a good linear relation between Io/I and the oxygen concentration in the aqueous solution.

EXAMPLE 8

The copolymer of MMA and Vbpy which was synthesized and purified in Example 1, and cis-dichlorobis(bipyridine)osmium complex which was synthesized by the known method (D. M. Klassen et al., J. Chem. Phys., 48, 1853 (1968)) were reacted in the same manner as in Example 1 to obtain the macromolecular complex E of the following formula:

A membrane was formed on quartz plate 1 using this macromolecular complex E in the same manner as in Example 1 to obtain an orange membrane of about 10 $\mu$m thick. This membrane was held in a cell for measurement of luminescence. The cell was filled with physiological saline, and the relation between the oxygen concentration and the luminescence intensity was investigated, in the same manner as in Example 1 except that an exciting ray having the wave length of 460 nm was used and measurement of the luminescence was conducted at the wave length of 600 nm. A linear relation was found between Io/I and the oxygen concentration. However, the luminescence intensity was lower and the slippage from a straight line was somewhat larger than the case in Example 1.

EXAMPLE 9

A 10 mmol/dm$^3$ aqueous solution of Ru(bpy)$_3$Cl$_2$ which had been synthesized and purified in Example 2 was prepared, and a filter paper (No.1, manufactured and sold by Toyo Filter Paper Co., Ltd.) was immersed therein, taken out after 30 minutes, washed with water and dried at room temperature for 24 hours to obtain a filter paper on which Ru(bpy)$_3$Cl$_2$ was adsorbed. This filter paper was cut into rectangle pieces of 40 mm long, 8 mm wide, which were fixed on a glass plate (40 mm long, 8 mm wide and 1 mm thick), and held in a cell for measuring luminescence in the same manner as in Example 1. A mixed gas of oxygen/argon prepared in arbitrary mixing ratios was introduced in the cell at 50 ml/min, the cell was tightly plugged 15 minutes thereafter, and the luminescence intensity in a mixed gas containing oxygen was measured, in the same manner as in Example 1 except that an exciting ray having the wave length of 460 nm and the luminescence was measured at the wave length of 605 nm. A good linear relation was obtained between Io/I and the oxygen concentration.

As seen from the foregoing, the probe for measuring oxygen concentration of the present invention is one which can be used even in a case where the exciting ray to be used therefor and the luminescence and visible rays, so that it is possible to use a flexible plastic fiber and the like as the conductor of light and also to use inexpensive materials for visible rays in the optical system. Further, the present probe can stably be used even when it is directly immersed in a solution and the like without a protective membrane such as an oxygen-permeable membrane, which makes miniaturization thereof easier.

What we claimed is:

1. A probe for measuring oxygen concentration by luminescence quenching, comprising a support made of a material that conducts visible light and an immobilized polypyridine metal complex film on said support, said film comprising:
    a metal selected from the group consisting of ruthenium, osmium, chromium, iridium, iron, cobalt and europium;
    a polypyridine ligand selected from the group consisting of bipyridine, phenanthroline, terpyridine and derivatives thereof for complexing with said metal to form the polypyridine metal complex, said polypyridine liqand having a polymerizable vinyl group; and
    means for immobilizing the polypyridine metal complex in the film, wherein said means is a macromolecule prepared by polymerizing said polypyridine ligand then reacting a metal complex to form the polypyridine metal complex.

2. The probe of claim 1, wherein said metal is selected from ruthenium and osmium.

3. The probe of claim 1, wherein said metal is ruthenium.

4. The probe of claim 1, wherein the polypyridine ligand is bypyridine.

5. The probe of claim 1, wherein the polypyridine metal complex is represented by the following formula:

wherein M is selected from the group consisting of ruthenium and osmium.

6. The probe of claim 1, wherein the macromolecule is prepared by copolymerizing a polypyridine ligand having a polymerizable vinyl group with a copolymerizable monomer and then reacting a metal complex to form the polypyridine metal complex.

7. The probe of claim 6, wherein the copolymerizable monomer is selected from the group consisting of styrene, methacrylic acid, acrylic acid and acrylonitrile.

* * * * *

UNITED STATES PATENT AND TRADEMARK OFFICE
CERTIFICATE OF CORRECTION

PATENT NO. : 5,128,102
DATED : July 7, 1992
INVENTOR(S) : MASAO KANEKO ET AL

It is certified that error appears in the above-indentified patent and that said Letters Patent is hereby corrected as shown below:

On the cover page, Item [22] PCT 102(e) date, change "1990" to --1989--.

Column 1, line 40, change "absobed" to --absorbed--.

Column 2, line 19, change "th" to --the--.

Column 3, line 8, change "plastic" to --plastics--.

Column 12, line 2, change "liqand" to --ligand--.

Signed and Sealed this

Twenty-ninth Day of March, 1994

Attest:

BRUCE LEHMAN

Attesting Officer      Commissioner of Patents and Trademarks